US005731304A

United States Patent [19]
Baer et al.

[11] Patent Number: 5,731,304
[45] Date of Patent: Mar. 24, 1998

[54] POTENTIATION OF TEMOZOLOMIDE IN HUMAN TUMOUR CELLS

[75] Inventors: John Colin Baer, London; Azadeh Alison Freeman, Croydon; Edward Stuart Newlands, London; Amanda Jean Watson, Godley Hyde; Joseph Anthony Rafferty, Edgeley Stockport; Geoffrey Paul Margison, Poynton, all of England

[73] Assignee: Cancer Research Campaign Technology, Regent's Park, England

[21] Appl. No.: 448,384

[22] PCT Filed: Jan. 13, 1994

[86] PCT No.: PCT/GB94/00065

§ 371 Date: Jun. 7, 1995

§ 102(e) Date: Jun. 7, 1995

[87] PCT Pub. No.: WO94/15615

PCT Pub. Date: Jul. 21, 1994

Related U.S. Application Data

[63] Continuation-in-part of Ser. No. 4,754, Jan. 14, 1993, which is a continuation-in-part of Ser. No. 781,020, Oct. 18, 1991, Pat. No. 5,260,291, which is a continuation-in-part of Ser. No. 607,221, Nov. 1, 1990, abandoned, which is a continuation of Ser. No. 456,614, Dec. 29, 1989, abandoned, which is a continuation of Ser. No. 338,515, Mar. 3, 1989, abandoned, which is a continuation of Ser. No. 135,473, Dec. 21, 1987, abandoned, which is a continuation of Ser. No. 40,716, Apr. 20, 1987, abandoned, which is a continuation of Ser. No. 885,397, Jul. 18, 1986, abandoned, which is a continuation of Ser. No. 798,365, Nov. 18, 1985, abandoned, which is a continuation of Ser. No. 712,462, Mar. 15, 1985, abandoned, which is a continuation of Ser. No. 586,635, Mar. 6, 1984, abandoned, which is a continuation of Ser. No. 410,656, Aug. 23, 1982, abandoned.

[51] Int. Cl.$^6$ ............................ A61K 31/33; A61K 31/52
[52] U.S. Cl. ........................................... 514/183; 514/262
[58] Field of Search ........................................ 514/183, 262

[56] References Cited

U.S. PATENT DOCUMENTS

| 4,536,386 | 8/1985 | Keenan . | |
|---|---|---|---|
| 5,091,430 | 2/1992 | Moschel et al. . | |
| 5,260,291 | 11/1993 | Lowt et al. | 514/183 |

FOREIGN PATENT DOCUMENTS

| 2932805 | 2/1981 | Germany . |
| 9113898 | 4/1991 | WIPO . |
| WO94/15615 | 7/1994 | WIPO . |

OTHER PUBLICATIONS

Dolan, M.E. et al., "Comparison of the inactiviation of mammalian and bacterial O$^6$-alkylguanine-DNA alkyltransferases by O$^6$-benzylguanine and O$^6$-methylguanine", Carcinogenesis, 12(12):2305–9 (1991).

Dolan, M.E. et al., "Effect of O$^6$-benzylguanine analogs on O$^6$-alkyltransferase activity and on the sensitivity of cells to alkylating agents", Proc. Annu. Meet Am. Assoc. Cancer Res., 32:A2227 (1990).

Moshel, R.C. et al., "Structural Features of Substituted Purine Derivatives Compatible with Depletion of Human O$^6$-Alkylguanine-DNA Alkyltransferase", J. Med. Chem., 35(23):4486–91 (1992).

Gonzaga, P.E. et al., "Evidence that covalent complex formation between BCNU–treated oligonucleotides ad E. coli alkyltransferases requires the O$^6$-alkylguanine function", Nucleic Acids Res., 18(13):3961–6 (1990).

Gonzaga, P.E. et al., "Formation of a covalent complex between BCNU–treated oligodeoxynucleotides and E. coli DNA alkyltransferase does not include the phosphotriester repair function", Proc. Annu. Meet Am. Assoc. Cancer Res., 31:A14, (1990).

Hammdan, M.A. et al., "Depletion of O$^6$-Alkylguanine-DNA alkyltransferase by O$^6$-benzylguanine in three-dimensional collagen cultures of normal human breast epithelial cells", Carcinogenesis, 13(10):1743–9 (1992).

Silber, J.R. et al., "O$^6$-Alkylguanine DNA–alkyltransferase is Not a Major Determinant of Sensitivity to 1,3-Bis(2-chloroethyl)-1-nitrosourea in Four Medulloblastoma Cell Lines", Oncol. Res., 4(6):241–8 (1992).

Gerson, S.L. et al., "Modulation of Nitrosourea Resistance in Human Colon Cancer by O$^6$-Methylguanine", Biochem. Pharmacol., 43:1101–7 (1992).

Bronstein, S.M. et al., "Efficient Repair of )$^6$-Ethylguanine, but not O$^4$-Ethylthymine or O$^2$-Ethylthymine, Is Dependent upon O$^6$-Alkylguanine-DNA Alkyltransferase and Nucleotide Excision Repair Activities in Human Cells", Cancer Res., 52(7):2008–11 (1992).

Pegg, A.E. et al., "Repair of DNA containing O$^6$-alkylguanine", FASEB J., 6(6):2302–10 (1990).

Lunn, J.M. et al., "Correlation between chemosensitivity of CB10-277 and O$^6$-alkyl-guanine-DNA alkyltransferase levels in human melanoma xenografts", Br. J. Cancer, 62(3): 514 (1990).

Hamdan, M.A. et al., "Depletion of O$^6$-alkylguanine-DNA alkyltransferase (AGT) activity of O$^6$-methylguanine and O$^6$-benzylguanine in collagen–cultured human breast epithelial cells", Proc. Annu. Meet Am. Assoc. Cancer Res., 33:A22 (1992).

Gersch, S.L. et al., "Inactivation of alkyltransferase by O$^6$-benzylguanine reverses BCNU resistance in a human colon cancer xenograft", Proc. Annul. Meet Am. Assoc. Cancer Res., 32:A2233 (1991).

Dolan, M.E. et al., "Depletion of O$^6$-Alkylguanine DNA Alkyltransferase (AGT) by Treatment of O$^6$-Benzylguanine (BG).", Proc. Annu. Meet Am. Assoc. Cancer Res., 31:A2682, (1990).

Dexter, E.U. et al., "Modulation of O$^6$-Alkylguanine-DNA Alkyltransferase in Rats following Intravenous Administration of O$^6$-Methylguanine", Cancer Res., 49(13:3520–4 (1989).

(List continued on next page.)

*Primary Examiner*—Jerome D. Goldberg
*Attorney, Agent, or Firm*—Klauber & Jackson

[57] ABSTRACT

The toxicity of temozolomide, an anti-tumour agent useful in the treatment of various mammalian neoplasms, can be potentiated by the prior administration of an ATase inhibiting agent, i.e., O$^6$-benzylguanine.

11 Claims, 5 Drawing Sheets

OTHER PUBLICATIONS

Schold, S.C., Jr. et al., "$O^6$–Alkylguanine–DNA alkyltransferase and sensitivity to procarbazine in human brain–tumor xenografts", J. Neurosurg., 70(4):573–7 (1989).

Gerson, S.L. et al., "Inactivation of $O^6$–alkylguanine–DNA alkyltransferase in human colan cancer: a model for biochemical modulation of tumor drug resistance", Proc. Annu. Meet. Am. Assoc. Cancer Res., 30:A2271 (1989).

Taverna, P. et al., "Influence of o–methylguanine on DNA damage cytotoxicity of temozolomide in L1210 mouse leukemia sensitive and resistant to chloroethylnitroxoureas":, Anticancer Drugs, 3(4): 401–5 (1992).

Dolan, M.E. et al., "Effect of $O^6$–benzylguanine on the sensitivity of human tumor xenografts to BCNU", Proc. Annu. Meet Am. Assoc. Cancer Res., 33:A2895 (1992).

Gorbacheve, L.B. et al., "$O^6$Methylguanine As A Modulator of Antitumor Activity of N–Alkyl–N–Nitrosoureas In Vito", Anticancer Drugs, 2(2):186–9 (1991) (Abstract only).

Dolan, M.E. et al., "Effect of $O^6$–Benzylguanine Analogues on Sensitivity of Human Tumor Cells to the Cytotoxic Effects of Alkylating Agents", Cancer Res., 51(13):3367–72 (1991).

Mitchell, R.B. et al., "Enhancement of Carmustine Activity By Inhibition of $O^6$–Alkylguanine–DNA Alkyltransferase with Dacarbazine or $O^6$–Benzylguanine", 39(3):747A (1991).

Maher, V.M. et al., "Effect of Inhibition of Repair of $O^6$–Methylguanine on Mutations Indued in Diploid Human Cells by Alkylation Agents", Proc. Annu. Meet Am. Assoc. Cancer Res., 32:A669 (1991).

Dolan, M.E. et al., "Modulation of Mammalian $O^6$–Alkylguanine–DNA Alkyltransferase in vivo by $O^6$–Benzylguanine and its Effect on the Sensitivity of a Human Glioma Tumor to 1–(2–chloroethyl)–3–(4–methylcyclohexyl)–1–nitrosourea", Cancer Commun., 2(11):371–7 (1990).

Avramis, V.I. et al., "Pharmacokinetics (PK) of $O^6$–methylguanine (O6MG) in CDF1 mice", Proc. Annu. Meet Am. Assoc. Cancer Res., 31:A2678 (1990).

Dolan, M.E. et al., "Depletion of $O^6$–alkylguanine–DNA alkyltransferase activity in mammalian tissues and human tumor xenografts in nude mice by treatment with $O^6$–methylguanine", Cnacer Chemther Pharmacol., 25(2):103–8 (1989).

Meer, L. et al., "Inhibition of the Hepatic $O^6$–Alkylguanine–DNA Alkyltransferase in vivo by Pretreatment with Antineoplastic Agents", Biochm. Pharmacol., 38(6):929–34 (1989).

Panella, T.J. et al., "Modulation of $O^6$–Alkylguanine–DNA Alkyltransferase–mediated Carmustine Resistance Using Streptoxzotocin: A Phase I Trial", Cancer Res., 52(9):2456–9 (1992).

Mitchell, R.B. et al., "Effect of temozolomide and dacarbazine on $O^6$–alkylguanine–DNA alkyltransferase activity and sensitivity of human tumor cells and xenografts to 1,3,–bis(2–chloroethyl)–1–mitrosourea", *Cancer Chemotherapy and Pharmacology,* 32:59–63 (1993).

Margison, G.P., "$O^6$–Alkylguanine–DNA–Alkyltransferase Gene Expression and the Cytoxicity of Triazenes", *Anti Cancer Res.,* 10(2 part A): 461 (1990).

Dolan et al., "Exposure of Hela Cells to $O^6$–Alkylguanines Increases Sensitivity to the Cytotoxic Effects of Alkylating Agents", Biophys. Res. Commun., vol. 132, pp. 178–185 (1985).

Dolan et al., "Depletion of Mammalian $O^6$–Alkylguanine–DNA Alkyltransferase Activity of $O^6$–Benzylguanine Provides a Means to Evaluate the Role of This Protein in Protection Against Carcinogenic and Therapeutic Alkylating Agents", Proc. Natl. Acad. Sci. U.S.A., vol. 87, pp. 5368–5372 (1990).

Fan et al., "Expression of a Human $O^6$–Alkylguanine–DNA–Alkyltransferase cDNA in Human Cells and Transgenic Mice", Nucleic Acid Res. vol. 18, pp. 5723–5727 (1990).

Gibson et al., "Combined Effects of Streptozotocin and Mitozolomide Against Four Human Cell Lines of the Mer* Phenotype", Cancer Res., vol. 46, pp. 4995–4998 (1986).

Lee et al., "$O^6$–Alkylguanine–DNA Alkyltransferase Depletion and Regeneration In Human Peripheral Lymphocytes Following Dacarbazine and Fotemustine", Cancer Res., vol. 51, pp. 619–623 (1991).

Morten et al., "Upregulation of $O^6$–Alkylguanine–DNA–Alkyltransferase Expression and the Presence of Double Minute Chromosones in Alkylating Agent Selected Chinese Hamster Cells", Carcinogenesis, Vo. 13, pp. 483–487 (1992).

Newlands et al., "Phase I Trial of Temozolomide (CCRG 81045:M&B 39831:NSC 362856)", Br. J. Cancer, vol. 65, pp. 287–291 (1992).

Skehan et al., "New Colorimetric Cytotoxicity Assay for Anticancer–Drug Screening", J. Natl. Cancer Inst., vol. 82, pp. 1107–1112 (1990).

Wasserman et al., "Use of a Colorimetric Microtiter (MTT) Assay in Determining the Radiosensitivity of Cells From Urine Solid Tumors", Int. J. Radiat. Oncol. Biol. Phys., vol. 15, pp. 699–702 (1988).

Wu et al., "Expression of Human $O^6$–Methylguanine–DNA Methyltransferase in a DNA Excision Repair–Deficient Chinese Hamster Ovary Cell Line and Its Response to Certain Alkylating Agents", Cancer Res., vol. 52, pp. 32–35 (1992).

Zlotogoski et al, "Pretreatment of Human Colon Tumour Cells With DNA Methylating Agents Inhibits their Ability to Repair Chloroethyl Monoadducts", Carcinogenesis, vol. 5, pp. 83–87 (1984).

Friedman et al., "Enhancement of Nitrosourea Activity in Medulloblastoma and Glioblastoma Multiforms", Journal of Natl. Cancer Institute, vol. 84, pp. 1926–1931 (1992).

D'Atri, S. et al., "Repair of DNA methyl Adducts and Sensitivity to Temozolomide of Acute Meylogenous Leukema AML Cells", Inst. Exp. Me. CNR, Rome Italy20 annual meeting of the International, Society for Experimental Hematology, Parma, Italy, Jul. 21–25, 1991 Exp Hematol (NY), 19(6):530.

Bronstein et al., "Modulation of Ethyinitrosourea–Induced Toxicity and Mutagenicity in Human Cells by $O^6$–Bezylguanine", Cancer Res. vol. 52, pp. 3851–3856 (1992).

Bull et al., "Antitumour Imidazotetrazines–XVI Macromolecular Alkylation by 3–Substituted Imidazotetrazinones", Biochem. Pharmacol., vol. 36 pp. 3215–3220 (1987).

Catapano et al., "In vitro and in Vivo Methazolastone–Induced DNA Damage and Repair in L–1210 Leukemia Sensitive and Resistant to Chloroethylnitrosoureas", Cancer Res., vol. 47, pp. 4884–4889 (1987).

Stevens, M.F. G. et al., "Antitumor Activity and Pharmacokinetics in Mice of 8-Carbamoyl-3-methyl-imidazo[5,1-di]-1,2,3,5-tetrazin-4(3H)-one (CCRG 81045; M&B 39831), a Novel Drug with Potential as an Alternative to Dacarbazine", Cancer Res., vol. 47, pp. 5846–5852 (1987).

Tsang, L.L.H. et al., "Comparison of the cytotoxicity in vitro of temozolomide and dacarbazine, prodrugs of 3-methyl-(triazen-1-yl)imidazole-4-carboxamide", Cancer Chemother Pharmacol. vol. 27, pp. 342–346 (1991).

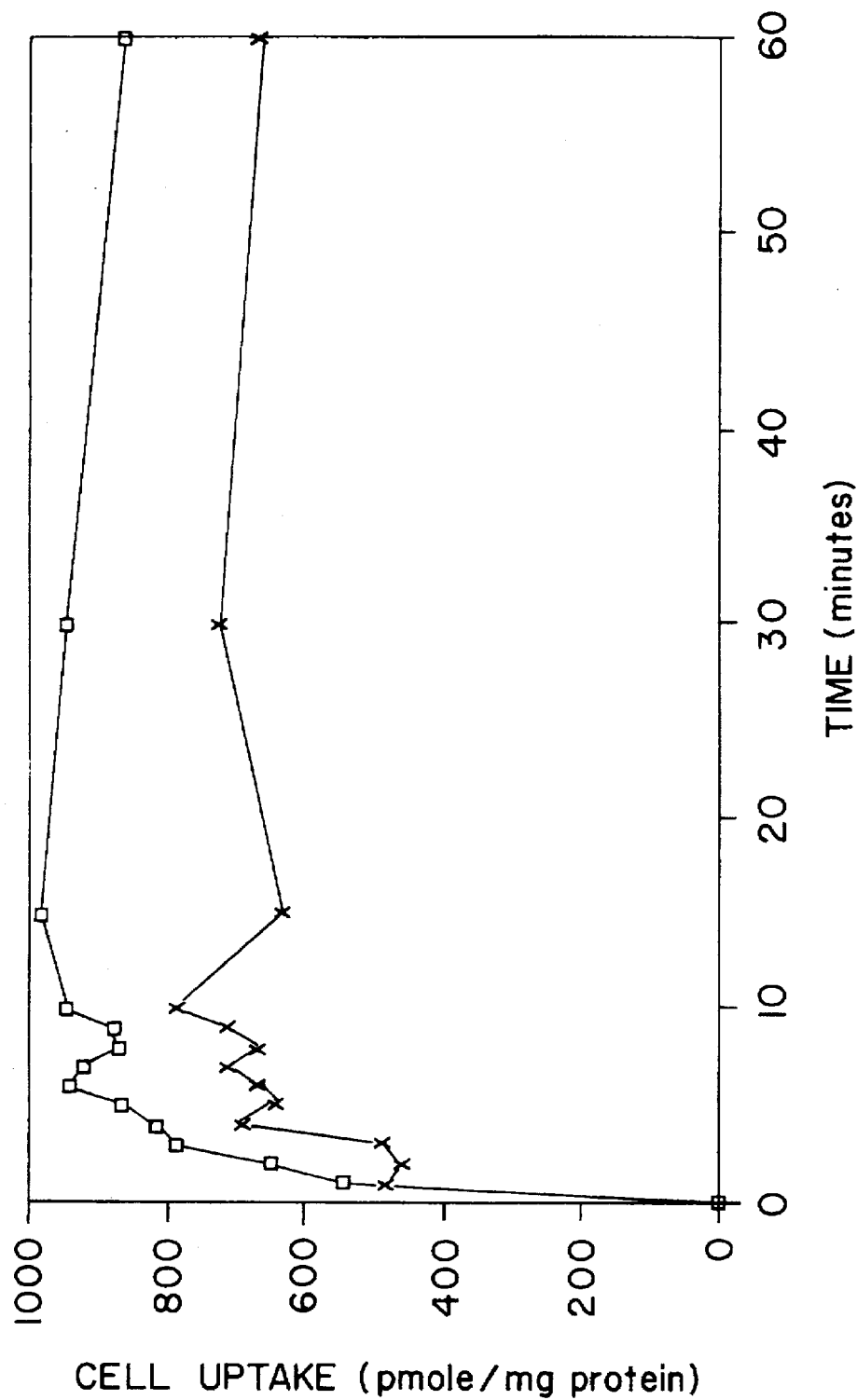

POTENTIATION OF TEMOZOLOMIDE IN HUMAN TUMOUR CELLS

This Application is a national phase entry of PCT application WO 94/156 which is a CIP of U.S. Ser. No. 08/004,754, filed Jan. 14, 1993, which is a continuation in part of U.S. Ser. No. 07/781,020, filed Oct. 18, 1991 now U.S. Pat. No. 5,260,191, which is a continuation in part of Ser. No. 607,221, Nov. 1, 1990, abandoned, which is a continuation of Ser. No. 456,614, Dec. 29, 1989, abandoned, which is a continuation of Ser. No. 338,515, Mar. 3, 1989, abandoned, which is a continuation of Ser. No, 135,473, Dec. 21, 1987, abandoned, which is a continuation of Ser. No. 40,716, Apr. 20, 1987, abandoned, which is a continuation of Ser. No. 885,397, Jul. 18, 1986, abandoned, which is a continuation of Ser. No. 798,365, Nov. 18, 1985, abandoned, which is a continuation of Ser. No. 712,462, Mar. 15, 1985, abandoned, which is a continuation of Ser. No. 586,635, Mar. 6, 1984, abandoned, which is a continuation of Ser. No. 410,656, Aug. 23, 1982, abandoned.

BACKGROUND OF THE INVENTION

Temozolomide, or 8-carbamoyl-3-methylimidazo[5,1-d]-1,2,3,5,-tetrazin-4-(3H)-one, (CCRG 81045, NSC 362856) has been found to possess valuable antitumour properties, see Newlands et al., Br. J. Cancer, 65: 287 (1992). In the clinic, temozolomide has shown activity against astrocytoma, gliomas, malignant melanoma and mycosis fungoides. The drug is most useful when administered according to a repeat dose schedule.

Methylated $O^6$-alkylguanine, e.g., from reaction with MTIC (the active methylating species of temozolomide), is repaired by the protein $O^6$-alkylguanine DNA alkyltransferase (ATase). Pretreatment of ATase-expressing cells with methylating agents (e.g., Zlotogoski et al., Carcinogenesis, 5:83, 1984; Gibson et el., Cancer Res., 46:4995, 1986), $O^6$-methylguanine (e.g., Dolan et al., Biophys. Res. Commun., 132:178 1985) or $O^6$-benzylguanine ($O^6$-BG, Dolan et al., Proc. Natl. Acad. Sci. U.S.A., 87:5368, 1990) has thus been shown to increase the cytotoxic effects of chloroethylating agents whilst little or no sensitization was observed in cells that do not express ATase.

Moschel, Dolan and Pegg, in U.S. Pat. No. 5,091,430, note that a transient decrease in ATase activity is all that is needed to enhance the effectiveness of chloroethylating agents. PCT published Application WO 91/13898 notes, for instance, a 3.8 fold decrease in the $ED_{50}$ for Me CCNU when combined with $O^6$-benzylguanine in SF767 cells. Thus, Moschel et al. show a general enhancement of the anti-neoplastic activity of an alkylating agent when used with a depletor of alkyltransferase.

Applicants' invention, which is surprising and unobvious in view of the earlier work, is that the chemotherapeutic effects of temozolomide can be dramatically potentiated (up to 300-fold for the MAWI cell line) by utilizing a particular dosing regimen which incorporates the administration of an ATase inhibitor. Thus, human cell cancers which were heretofore insusceptible or only mildly susceptible to temozolomide therapy can be treated by the combination of temozolomide with an ATase inhibitor.

Accordingly, it is a principal object of the present invention to provide compositions and methods for improving and extending the therapeutic usefulness of temozolomide as an antineoplastic agent by a combination therapy with a potentiator which is an inhibitor of the enzyme $O^6$-alkylguanine DNA alkyltransferase (ATase).

It is a further object of the present invention to provide therapeutic regimens using these compositions and methods for the optimal potentiation of toxicity of temozolomide to human cancer cells.

It is a still further object of the present invention to provide a repeat dosing regimen of temozolomide which is potentiated by prior or concomitant administration of an ATase inhibitor.

It is a still further object of the present invention to provide a method of determining the relative potentiation of temozolomide toxicity by an ATase inhibitor of a particular human cancer cell by ascertaining the amount of ATase produced by said cancer cell.

SUMMARY OF THE INVENTION

The present invention relates to the potentiation of temozolomide toxicity in human cancer cells using inhibitors of $O^6$-alkylguanine DNA alkyltransferase (ATase). Further, a dosage regimen for optimal therapy, and methods of identifying potentially temozolomide-sensitive human cancer cells, are provided.

BRIEF DESCRIPTION OF THE DRAWINGS

FIG. 5 is a graph of uptake of radiolabel at 4° C. by cells treated with $^{14}C$-temozolomide. MAWI (■), ZR-75-1 (x).

DETAILED DESCRIPTION OF THE INVENTION

Figure 1:
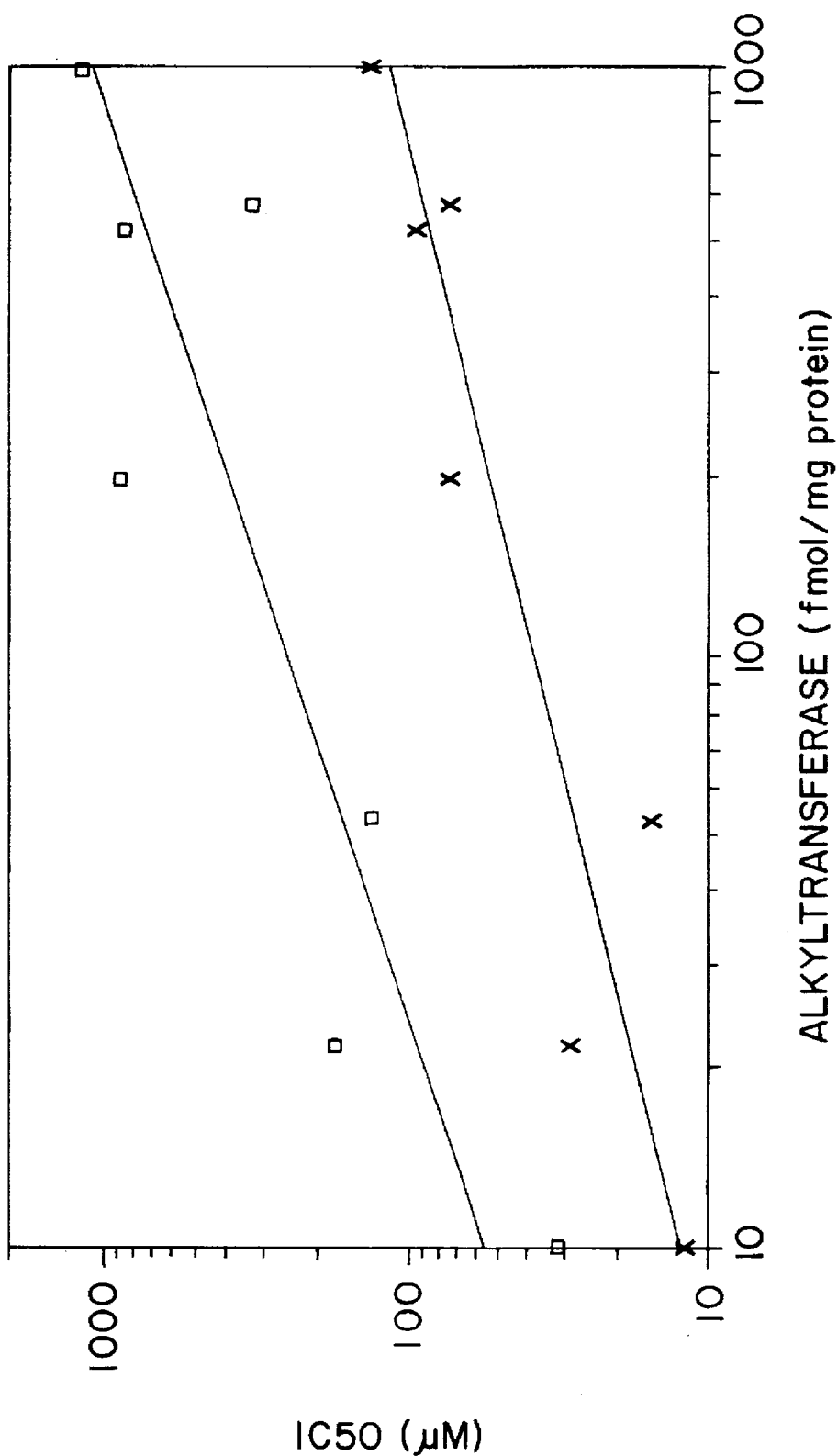
FIG. 1 is a graph of the cytotoxicity ($IC_{50}$) of temozolomide (■) and CCNU (x) versus cellular Atase levels in the human tumour cell lines (in order of increasing ATase levels): ZR-75-1, U87MG, U373, LS174T, LOVO, MCF-7 and MAWI.

The toxicity of temozolomide, an antitumour agent useful in the treatment of human cancers, can be greatly enhanced by its use in conjunction with a potentiator which is an inhibitor of the enzyme $O^6$-alkylguanine DNA alkyltransferase (ATase). More particularly, the use of ATase inhibitors, such as $O^6$-benzylguanine (BG), can enhance the toxicity of temozolomide, in, for example, the MAWI cell line, by up to about 300 fold when utilized in the scheduled dosage regimen of the present invention and enable the use of temozolomide in the chemotherapy of human cancers heretofore insusceptible or only mildly susceptible to such therapy.

A parallel toxicity for temozolomide and lomustine (CCNU) (after 1 hour drug exposure), can be shown with a number of human tumour cell lines, correlating with their ATase content. Methylation of the $O^6$-position of guanine in DNA by temozolomide thus results in a cytotoxic lesion. By screening human cancer cells for their relative ATase production, sensitivity to temozolomide can be determined. A cell producing high amounts of ATase will thus be less sensitive to temozolomide alone than one producing minimal ATase levels.

Pretreating cells with a single dose of BG causes a modest (<4 fold) increase in temozolomide toxicity. The degree of enhancement for temozolomide and lomustine (CCNU) are a similar order of magnitude. In a colony assay, human ATase cDNA-transfected fibroblasts pretreated with BG remained more resistant to temozolomide than control transfected fibroblasts, although the ATase protein was eliminated. This is unlikely to be due to differences in temozolomide transport and may simply reflect resynthesis of ATase by the phAT fibroblasts to diminish the effect of pretreatment with the inhibitor.

However, most surprisingly, a major potentiation of temozolomide toxicity (up to about 300 fold) by BG has been found in the MAWI cell line after five days treatment. A similar degree of enhancement was seen in MCF-7 cells which also contain high levels of ATase, but only a small effect in U373 cells which have low levels. The results in the testing of the MAWI and MCF-7 cell lines imply that the continued presence of the ATase inhibitor permits a build up of DNA damage.

The present invention thus provides a method of potentiating the toxicity of temozolomide in human cancer cells by administering an ATase inhibiting amount of an ATase inhibitor, and a product comprising temozolomide and an ATase inhibitor as a combined preparation for simultaneous, separate or sequential administration in said treatment of human cancer cells.

Preferably, this administration of an ATase inhibitor is repeated over a period of several or multiple days, and is prior to the administration of the doses of temozolomide. Repeat doses can be administered at 1, 2, 3, 4 or 5 days, with 4 or 5 days being the preferred period of therapy.

Further, and most preferably, the temozolomide is administered to a patient in repeat doses over a period of days, and an ATase inhibiting amount of an ATase inhibitor is administered prior to each dose of temozolomide, resulting in a markedly increased toxicity of the temozolomide to human cancer cells, e.g., about 300 fold for the MAWI cell line.

In a preferred embodiment, the ATase inhibitor is administered in an ATase inhibiting amount, i.e., an amount sufficient to sensitize the tumour in vivo without causing undue sensitization of normal tissue, when the ATase inhibitor is used concurrently with temozolomide.

The amount of ATase inhibitor employed in the present invention to be used varies according to the degree of the effective amount required for treating tumour cells. A suitable dosage is that which will result in a concentration of the ATase inhibitor in the tumour cells to be treated which results in the depletion of the ATase activity, e.g., about 1–2000 mg/kg, and preferably about 10–800 mg/kg, prior to chemotherapy.

The neoplasms for which temozolomide is a particularly suitable treatment include carcinomas, melanomas, sarcomas, lymphomas and leukaemias, with specific utility for astrocytoma, gliomas, malignant melanoma, and mycosis fungoides, Ewings sarcoma, chronic lymphocytic leukaemia, and lung and breast tumours. Particularly dramatic enhancement of the temozolomide activity with an ATase inhibitor is found in breast, astrocytoma and colorectal tumour cells.

Typical dosage ranges of temozolomide are generally between 0.1 and 200, preferably between 1 and 20, mg/kg body weight per day, or expressed in terms of body surface area, about 40–400, and preferably about 150–300 mg/m$^2$ per day.

The amount of potentiation by the ATase inhibitor is dependent upon the amount of ATase normally present in the particular cancer cell type. A cancer cell having higher levels of ATase will be potentiated more dramatically by the preadministration of the ATase inhibitor.

The ATase inhibitor utilizable in the present invention are those known to possess such activity, for instance, the $O^6$-alkylguanines such as $O^6$-methylguanine, the alkenylguanines such as $O^6$-allylguanine and the $O^6$-arylguanines, such as $O^6$-benzylguanine and the $O^6$-benzylated guanine, guanosine and 2'-deoxyguanosine compounds described in PCT International Application WO 91/13898 (published Sep. 19, 1991). Particularly suitable for use in the present invention is $O^6$-benzylguanine.

The particular dosage of ATase inhibitor depends upon the amount of ATase normally found in the cancer cell being treated, the age and condition of the patient, and the particular ATase inhibitor being utilized.

Temozolomide has been found to be most preferably administered in repeat dosages on consecutive days, and the dramatic potentiation effects of the present invention are realized in the highly preferred regimen involving the administration of an ATase inhibiting dose of the ATase inhibitor prior to, or concurrent with, the administration of each dose of temozolomide administered. Preferably, $O^6$-benzylguanine is utilized as the ATase inhibitor, along with temozolomide administered at a daily rate of 150–300 mgm$^{-2}$ in four or five divided doses over four or five consecutive days (total dose 750–1500 mg/m$^2$). Preferably, each dose of the ATase inhibitor is administered 2–8 hours prior to each dose of the temozolomide. This affords the greatest potentiation of temozolomide toxicity, and results in the most effective treatment of the patient's particular neoplasm. Most preferably, this regime is repeated after an interval of about four (4) weeks.

An alternate dosage schedule for the administration of temozolomide with $O^6$-benzylguanine is a continuous schedule wherein the two drugs are administered on a daily basis for a period of four (4) or more days. This combination therapy can be extended as needed on a continual basis until remission is attained.

Additionally, the ATase production of a particular human cancer cell can be utilized as a screening method to determine potentiation of temozolomide toxicity to said cell. In a preferred method, the ATase content of the particular cell line is assayed, e.g., by the method described by Lee et al., *Cancer Res.*, 51: 619 (1991), and the potential sensitivity to temozolomide determined. Such a determination then enables the appropriate combination of temozolomide and ATase inhibition to be administered in a therapeutic regimen.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g., magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg to 500 mg, according to the particular application.

The actual dosage employed may be varied depending upon the requirements of the patient and the severity of the condition being treated. Determination of the proper dosage for a particular situation is within the skill of the art. For convenience, the total daily dosage may be divided and administered in portions during the day, if desired. Temozolomide may be administered using conventional techniques such as those described in Wasserman et al., *Cancer,* 36: 1258–1268 (1975). Where appropriate, oral administration at a rate of 40–400 mgm$^{-2}$ per day, and preferably 150–300 mgm$^{-2}$ per day, in 1–5, and preferably 4–5 doses, over 1–5, and preferably 4–5, consecutive days is highly preferred. Intravenous administration at a daily dose of 25–250 mgm$^{-2}$ is preferable for a continuous dosing therapy regimen. Oral administration can be utilized for a repeat dosing regimen.

The ATase inhibitor can be administered separately prior to, or concurrent with, the temozolomide. Where it is desirable to do so, both the ATase inhibitor and temozolomide can be combined into a unit dosage form to facilitate patient dosing. Such combination dosage forms may be in any of the above-described dosage forms, but, as noted above, are preferably in oral or intravenous forms.

The temozolomide and the ATase inhibitor can be packaged in a kit form. In such a kit, the temozolomide and the ATase inhibitor would be individually formulated into particular dosage forms for the particular route of administration, and contain instructions for the administration of the contents. In a typical embodiment for oral formulation, such a kit may be in the form of a blister package with separately formulated oral dosage forms of the temozolomide and the ATase inhibitor.

Any necessary adjustments in dose can be readily made to meet the chemotherapeutic treatment requirements of the individual patient and adjusted accordingly by the skilled practitioner.

The invention disclosed herein is exemplified by the following preparative examples, which should not be construed to limit the scope of the disclosure.

EXAMPLE 1

Materials and Methods

Materials

Tissue culture medium was purchased from ICN Biomedicals Ltd. (High Wycombe, UK) and fetal calf serum from Gibco Ltd (Paisley, UK). O$^6$-benzylguanine (BG) was kindly supplied by Dr. R. C. Moschel (NCI-Frederick Cancer Research & Development Center, Frederick, Md., USA). Temozolomide and its chloroethyl analogue, mitozolomide (8-carbamoyl-3-(2-chloroethyl) imidazo[5,1-d]-1,2,3,5-tetrazin-4-(3H)-one), were synthesized by May and Baker Ltd (Dagenham, UK) and stored as solutions in DMSO at −70° C. All other chemicals were purchased from Sigma Chemical Co. Ltd. (Poole, UK).

Cytotoxicity studies

Cell lines were routinely grown as monolayers in DMEM supplemented with 10% foetal calf serum, 25 mM HEPES, glutamine and penicillin/streptomycin. Cytotoxicity studies were carried out in HEPES-free medium in a 5% $CO_2$ atmosphere. 750–1000 cells/well were plated in 96 well plates and, after overnight incubation, were treated for 2 hours with or without 33 µM BG. Temozolomide or CCNU was then added for 1 hour in the same medium, the final DMSO concentration not exceeding 1%. The cells were grown for a further 7 days in fresh medium and assayed for protein content by NCI sulphorhodamine assay described by Skehan et al., *J. Natl. Cancer Inst.,* 82: 1107 (1990); growth studies showed that cells were in log phase growth during the assay period. For the repeat temozolomide dosing schedule, cells were given consecutive 24 hour treatments, with fresh medium each day. Assays were carried out at least in duplicate.

Human ATase cDNA-transfected or control XP cells [Fan et al., *Nucleic Acid. Res.,* 28: 5723 (1990)] were grown in MEM and 1000 cells/well were plated. After a 3 hour incubation, temozolomide, freshly diluted into MEM, was added and the plates incubated for 5 days. Survivals were assayed as described by Morten et al., *Carcinogenesis,* 13: 483 (1992). In the BG experiments, 300 cells were plated in triplicate onto 9 cm plates and allowed to attach for 5 hours. BG was added (10 µM in MEM) 3 hours prior to the treatment with temozolomide which was freshly diluted into MEM containing 10 µM BG. After 7 days, colonies were strained with Giemsa and counted.

O$^6$-alkylguanine DNA alkyltransferase assay

This assay was carried out as described by Lee et al., *Cancer Res.,* 51: 619 (1991). Thus, varying amounts of cell extracts are incubated with DNA which contains O$^6$-methylguanine labelled with [$^3$H] in the methyl group, at preferably 37° C. for 2 hours in a total volume of 300 µl of 1 mg/ml of bovine serum albumin in buffer 1. After incubation, bovine serum albumin (100 µl of a 10 mg/ml solution in buffer 1) and perchloric acid (100µl of a 4M solution) are added in rapid succession. A further 2 ml of 1M perchloric is added and the mixture heated at 75° C. for 40 minutes to degrade the DNA to acid soluble material. The protein, which contains the methylated ATase, is then collected by centrifugation, washed with 4 ml of 1M perchloric acid before being resuspended in 300 µl of 0.01M sodium hydroxide and dissolved in 3 ml of aqueous scintillation fluid (Ecoscint A: National Diagnostics), and counted. The protein content of the cells was determined with a BioRad protein assay kit using bovine serum albumin as a standard. ATase activity is expressed as fmol methyl transferred to protein per mg of total protein in the extract.

Cellular uptake of [$^{14}$C]—labelled temozolomide 8-carbamoyl-3-[$^{14}$C]methylimidazo[5,1-d]-1,2,3,5-tetrazin-4-(3H)-one (specific activity 26.3 mCi/mmole) was kindly supplied by Dr. John Slack (Aston Molecules Ltd, Birmingham, UK). Cell suspensions (5×10$^6$/ml) were equilibrated at 4° C. and treated with 200 µM of the labelled drug.

10⁶ cells were pipetted into eppendorf tubes and centrifuged through 250 ul of an oil mixture (4:1 "Three-in-One"/Dow Corning silicone oil). The aqueous layer was aspirated and the oil layer gently washed with a further 300 μl of saline. After centrifugation both layers were aspirated, the cell pellet dissolved in a tissue solubilizer such as Protosol® (quaternary ammonium hydroxide in toluene) and added to scintillation vials containing Optiphase® (95–99% diisopropylnaphthalene).

Results of Cytotoxicity studies

The data are given below in Table I.

Figure 2:
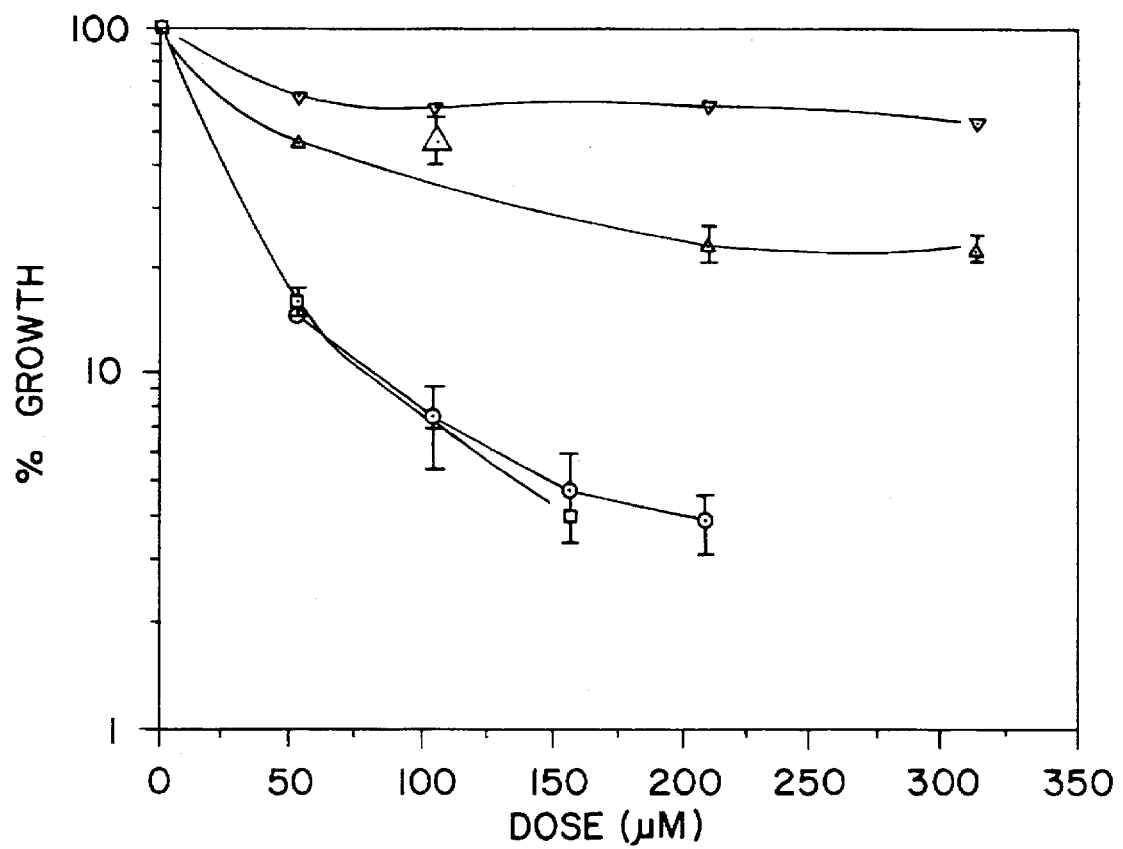
FIG. 2 is a graph of the cytotoxicity of temozolomide in pZipneoSV(X) 1-transfected (○,■) or phAT-transfected (▼,▲)XP-derived cell lines in the presence (■,▲) or absence (○,▼) of 10 µM BG. Error bars indicate +/−1 s.d.

The control XP cells (xeroderma pigmentosa cells transfected with pZipneoSV(X) 1 (Fan et al., *Nucleic Acids Res.*, 18: 5723, 1990), which express barely detectable levels of ATase, are 4–5 fold more sensitive to temozolomide or the CCNU-related agent mitozolomide than the human ATase cDNA-transfected cells (see Table I). In a colony forming assay for the cytotoxicity of temozolomide (see FIG. 2), BG pretreatment showed a similar degree of potentiation for the human ATase-transfected XP cells as for the tumour cells, but had no measurable effect on the control XP cells, which do not express ATase. Although BG depleted the ATase

TABLE I

Single Dose Cytotoxicity

| | TEMOZOLOMIDE | | | CCNU | | | |
|---|---|---|---|---|---|---|---|
| CELL LINE | $IC_{50}$ [−BG] (μM) | $IC_{50}$ [+BG] (μM) | Ratio[1] | IC50 [−BG] (μM) | IC50 [+BG] (μM) | Ratio[1] | ATase (fmol/mg protein) |
| BREAST | | | | | | | |
| ZR-75-1 | 32 | 23 | 1.4 | 12 | 25 | 0.5 | <10 |
| MCF-7 | 325 | 171 | 1.9 | 70 | 31 | 2.2 | 581.3 |
| ASTROCYTOMA | | | | | | | |
| U87MG | 172 | 131 | 1.3 | 28 | 8.8 | 3.2 | 21.9 |
| U373 | 131 | 78 | 1.7 | 15 | 12 | 1.2 | 53.2 |
| COLORECTAL | | | | | | | |
| LS174T | 873 | 632 | 1.4 | 73 | 13 | 5.7 | 199.6 |
| LOVO | 848 | 323 | 2.6 | 92 | 32 | 2.9 | 529.0 |
| MAWI | 1173 | 335 | 3.5 | 133 | 30 | 4.4 | 992.3 |
| XP LINES | | | | | | | |
| pZip | 23[2] | — | — | (0.8)[2,3] | — | — | <2 |
| phAT | 100[2] | — | — | (4.2)[2,3] | — | — | 1240 |

Cells were exposed in tissure culture to +/− $O^6$-benzylguanine (BG) prior to a single dose of Temozolomide or CCNU.
[1]$IC_{50}$ [−BG]/$IC_{50}$ [+BG].
[2]Results obtained by MTT assay of Wasserman et al., *Int. J. Radiat. Oncol. Biol. Phys.*, 15:699 (1988).
[3]Figures in parentheses refer to mitozolomide.

The data of Table I which are graphically displayed in FIG. 1 show a reasonable correlation between the sensitivity (as measured by the concentration which gives 50% of growth or $IC_{50}$) of tumour cell lines to temozolomide (r=correlation coefficient=0.87) or CCNU (r=correlation coefficient=0.92) and their ATase content. The slopes are nearly parallel except that CCNU is approximately five times more toxic on a molar basis. One exception was the MCF-7 line which is moderately sensitive to temozolomide and has a relatively high ATase activity. Cell lines pretreated with a non-toxic dose of BG were up to 3.5 fold more and 6 fold more sensitive to temozolomide and CCNU respectively.

activity in the former cells (see below), they remained more resistant to temozolomide than the control pZip transfected fibroblasts.

The repeated dosing schedule data are given below in Table II.

TABLE II

Repeated Dose Temozolomide Cytotoxicity [$IC_{50}$ (μm)]

| CELL LINE | DAY 1 | | DAY 2 | | DAY 3 | | DAY 4 | | DAY 5 | |
|---|---|---|---|---|---|---|---|---|---|---|
| | −BG | +BG | −BG | +BG | −BG | +BG | −BG | +BG | −BG | +BG |
| U373 | | | | | | | 51 | 18 | | |
| MAWI | 319 | 196 | 350 | 59 | 383 | 21 | 383 | 7.2 | 326 | 1.0 |
| MCF-7 | 319 | 89 | 319 | 51 | 375 | 11 | | | | |

Cells were exposed in tissue culture to +/− $O^6$-benzylguanine (BG) prior to repeated daily doses of temozolomide.

Figure 3:
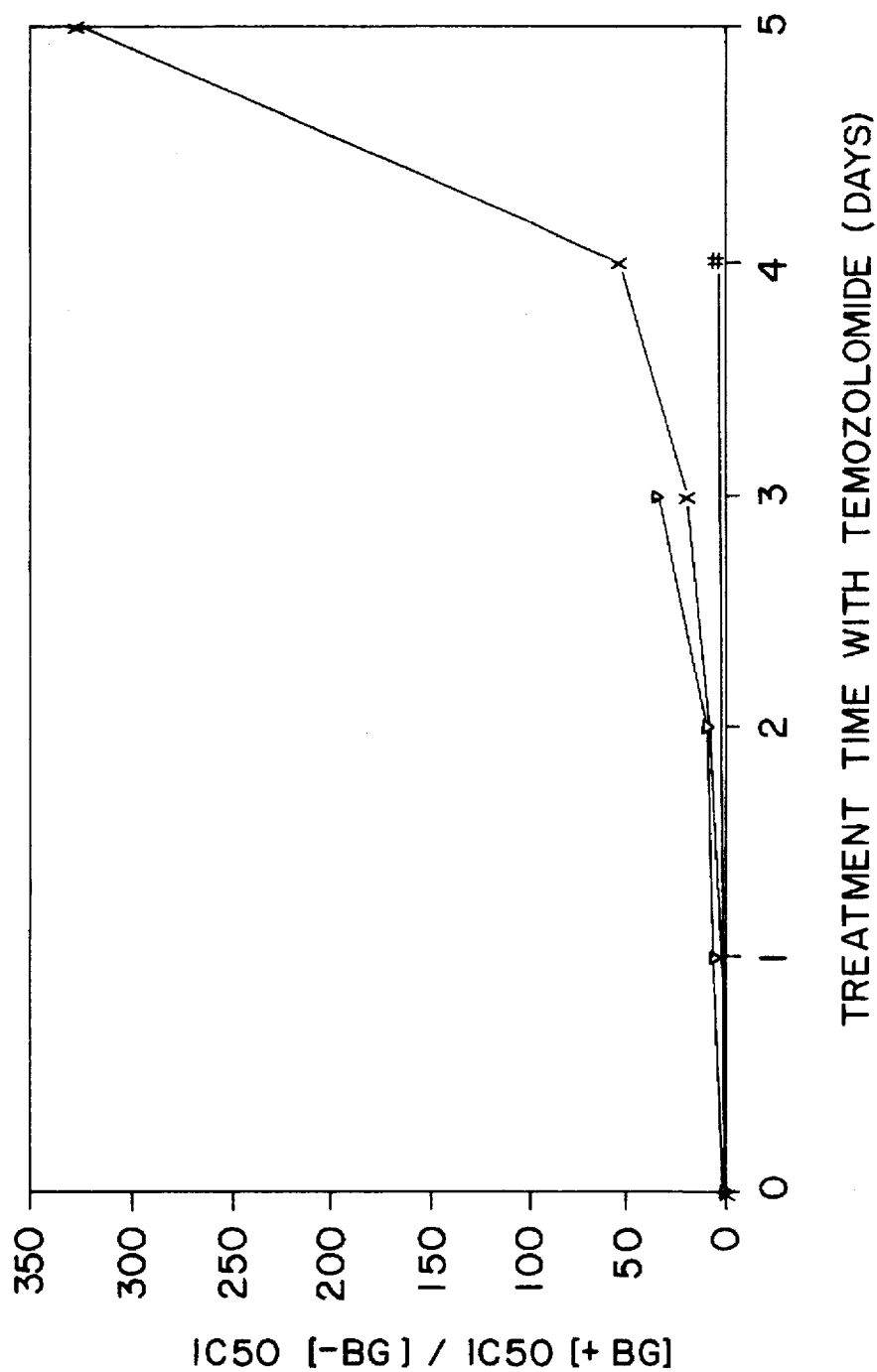
FIG. 3 is a graph of the cytoxicity ratio of repeated daily doses of temozolomide in MAWI (x), MCF-7 (▼) or U373 (#) human tumour cell lines of drug only, $IC_{50}$ (−BG), compared to preincubation with BG, $IC_{50}$ (+BG).

The repeated dosing schedule showed dramatic potentiation of temozolomide toxicity by BG in MAWI and MCF-7 cells (see also FIG. 3).

After treatment with five 24 hour doses, the MAWI cell line was over 300 fold more sensitive to temozolomide when BG was present. Multiple doses of temozolomide, by itself, were not more toxic than a single 24 hour dose in either cell line. In a similar experiment on U373 cells, which have a low level of ATase, the presence of BG caused only a 3 fold potentiation, after four 24 hour doses.

Alkyltransferase levels

The concentrations of BG used rapidly reduced to an undetectable level the initially high ATase content of MAWI cells and human ATase cDNA transfected XP fibroblasts. HPLC analysis showed that BG was stable in tissue culture medium for at least 24 hours at 37° C.

Figure 4:
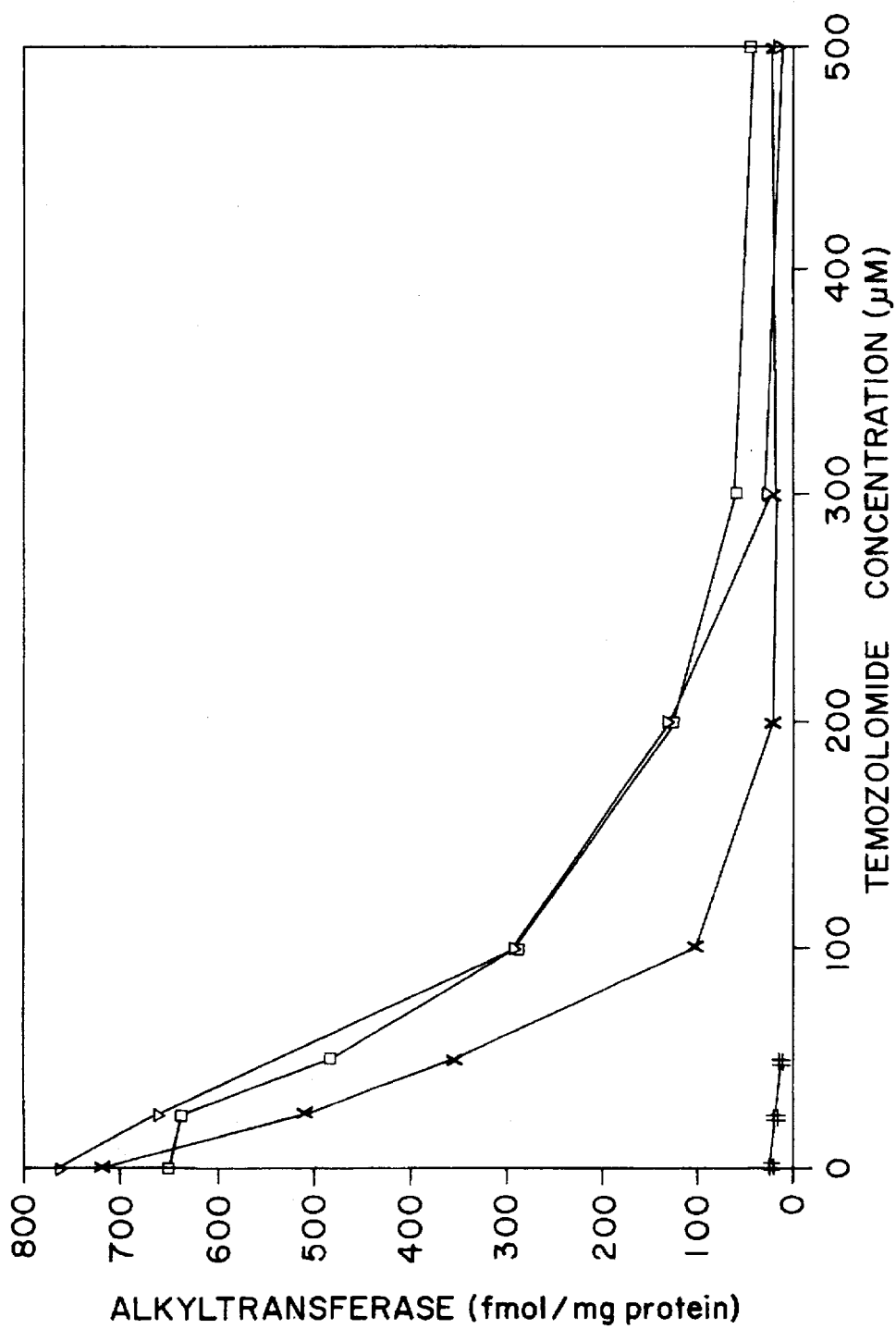
FIG. 4 is a graph of the effect of increasing concentrations of temozolomide on ATase levels in the human tumour cell lines: LOVO (■), MAWI (x), MCF-7 (▼), U373 (#).

Temozolomide, following a three-hour incubation, was found to cause a decrease in ATase content of U373, MCF-7, LOVO and MAWI cell lines. There was a 50% reduction at 50–100 μM for each line (see FIG. 4), despite a 3–4 fold difference in the single dose temozolomide cytotoxicity between MCF-7 and the colorectal lines (LOVO and MAWI). A similar reduction was found in the more sensitive U373 line, although the ATase levels were close to the detection limit of the assay.

To eliminate the possibility of differences in temozolomide transport, the cell uptake of the [$^{14}$C]-labelled compound was studied by the most sensitive and resistant cell lines (ZR-75-1 and MAWI, respectively). The results shown in FIG. 5 show that uptake was very rapid at 4° C., being complete within 5 minutes in both cell lines. Similar amounts of drug were found in both cell lines when adjusted for protein concentration. Rapid uptake at 4° C. was consistent with passive diffusion of temozolomide previously shown in two lymphoid lines by Bull et al., *Biochem. Pharmacol.*, 36: 3215, (1987).

EXAMPLE 2

| Oral Formulation | mg. per Capsule |
|---|---|
| Temozolomide | 100 |
| Lactose, USP | 213 |
| Microcrystalline Cellulose | 30 |
| Sodium lauryl sulfate | 20 |
| Corn starch | 25 |
| Magnesium stearate | 2 |

Mix together the temozolomide and lactose, microcrystalline cellulose, sodium lauryl sulfate and corn starch. Pass through a No. 80 screen. Add magnesium stearate, mix and encapsulate into the proper size two-piece gelatin capsule.

EXAMPLE 3

| Oral Formulation | mg. per Capsule |
|---|---|
| $O^6$-benzylguanine | 100 |
| Lactose, USP | 213 |
| Microcrystalline Cellulose | 30 |
| Sodium lauryl sulfate | 20 |
| Corn starch | 25 |
| Magnesium stearate | 2 |

Mix together the $O^6$-benzylguanine, lactose, microcrystalline cellulose, sodium lauryl sulfate and corn starch. Pass through a No. 80 screen. Add magnesium stearate, mix and encapsulate into the proper size two-piece gelatin capsule.

EXAMPLE 4

| Oral Formulation | mg. per Capsule |
|---|---|
| Temozolomide | 100 |
| $O^6$-benzylguanine | 100 |
| Lactose, USP | 213 |
| Microcrystalline Cellulose | 30 |
| Sodium lauryl sulfate | 20 |
| Corn starch | 25 |
| Magnesium stearate | 2 |

Mix together the temozolomide and $O^6$-benzylguanine, lactose, microcrystalline cellulose, sodium lauryl sulfate and corn starch. Pass through a No. 80 screen. Add magnesium stearate, mix and encapsulate into the proper size two-piece gelatin capsule.

EXAMPLE 5

| Intravenous Formulation | mg/ml |
|---|---|
| Temozolomide | 100 |
| Sodium Bisulfite, USP | 3.2 |
| Disodium Edetate, USP | 0.1 |
| Water for Injection, q.s. ad | 1.0 ml |

EXAMPLE 6

| Intravenous Formulation | mg/ml |
|---|---|
| Temozolomide | 100 |
| $O^6$-benzylguanine | 100 |
| Sodium Bisulfite, USP | 3.2 |
| Disodium Edetate, USP | 0.1 |
| Water for Injection, q.s. ad | 1.0 ml |

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A method of potentiating the toxicity of temozolomide in human cancer cells by administering to a patient in need of such therapy an ATase inhibiting amount of $O^6$-benzylguanine and an effective amount of temozolomide.

2. The method of claim 1 wherein said $O^6$-benzylguanine is administered prior to the administration of said temozolomide.

3. The method of claim 1 wherein the dosage administered of said $O^6$-benzylguanine is about 1–2000 mg/kg of patient body weight.

4. The method of claim 1 wherein the dosage administered of the $O^6$-benzylguanine is 10–800 mg/kg of patient body weight.

5. The method of claim 4 wherein the temozolomide is administered at a rate of 150–300 mgm$^{-2}$ of body surface area per day.

6. The method of claim 1 wherein said ATase inhibitor is administered in a dose of 10–800 mg/kg of patient body weight prior to the administration of the temozolomide, said temozolomide is administered in an amount of 150–300 mgm$^{-2}$ of body surface area per day, and said O$^6$-benzylguanine and said temozolomide are administered in divided doses on consecutive days.

7. The method of claim 6 wherein the total dose of temozolomide is divided into at least four individual doses which are administered on at least four consecutive days.

8. The method of claim 7 wherein said O$^6$-benzylguanine is administered two to eight hours prior to the administration of said temozolomide.

9. The method of claim 1 wherein said O$^6$-benzylguanine and said temozolomide are administered in divided doses on consecutive days.

10. A method according to claim 1 wherein the human cancer cells are breast cancer tumour cells, astrocytoma tumour cells, colorectal tumour cells, melanoma rumour cells, mycosis fungoides tumour cells or glioma tumour cells.

11. A pharmaceutical composition, for use in treating human cancer cells in a patient in need of such treatment, comprising an effective amount of an O$^6$-benzylguanine and an effective amount of temozolomide.

* * * * *